United States Patent [19]

Epstein

[11] Patent Number: 4,724,213
[45] Date of Patent: Feb. 9, 1988

[54] MURINE HYBRIDOMA LYM-1 AND DIAGNOSTIC ANTIBODY PRODUCED THEREBY

[75] Inventor: Alan L. Epstein, LaCanada, Calif.

[73] Assignee: Northwestern University, Evanston, Ill.

[21] Appl. No.: 738,084

[22] Filed: May 25, 1985

[51] Int. Cl.$^4$ .................. C12N 5/00; C07K 15/04
[52] U.S. Cl. .................. 435/240.27; 435/7;
　　435/68; 435/172.2; 530/387; 424/1.1; 424/9;
　　424/85; 935/104; 935/107; 935/110
[58] Field of Search .................. 435/240, 68, 7, 172.2;
　　260/112 R; 935/104, 107, 110; 530/387;
　　424/1.1, 9, 85

[56] References Cited

U.S. PATENT DOCUMENTS 4,513,088 4/1985 Levy et al. .................. 435/68

OTHER PUBLICATIONS

Marder, R. J. et al, Lab. Investig., 52(5): 497–504 (1985), cited in Bio. Abstract 80051070.
Epstein, A. L. et al, J. Immunology, 133(2): 1028–1036 (1984), cited in Bio. Abstract 78093014.
Murray, L. J. et al, Clin. Exper. Immunol. 59(2): 315–326 (1985), cited in Bio. Abstract 80005120.
Takami, T. et al, J. Immunology, 134(2): 828–834 (1985), cited in Bio. Abstract 79086651.
Jephthah, J. et al, Blood, 63(2): 319–325 (1984), cited in Bio. Abstract 78003585.
Knowles, D. M. et al, Blood, 62(1): 191–199 (1983), cited in Bio. Abstract 77045013.
Gobbi, M. et al, Brit. J. Haematol., 54(3): 393–404 (1983), cited in Bio. Abst. 77028588.

Primary Examiner—Margaret Moskowitz
Attorney, Agent, or Firm—Tilton, Fallon, Lungmus & Chestnut

[57] ABSTRACT

Hybridoma Lym-1 (ATCC No. HB 8612) produces murine IgG2a monoclonal antibodies specifically against normal human B cells and derived malignancies. The Lym-1 antibodies have clinical utility for the in vivo diagnosis of human B-cell lymphomas and leukemias.

2 Claims, No Drawings

MURINE HYBRIDOMA LYM-1 AND DIAGNOSTIC ANTIBODY PRODUCED THEREBY

This invention was made in the course of research supported in part by a grant from the National Institutes of Health (NIH R01-CA30621).

FIELD OF INVENTION

The field of the invention is hybridomas and monoclonal antibodies. More specifically, this invention relates to hybridoma-produced monoclonal antibodies which identify B-lymphocyte surface antigens, and which are useful in the diagnosis and therapy of B-cell derived human lymphomas and leukemias.

BACKGROUND AND PRIOR ART

The fusion of mouse myeloma cells and spleen cells from immunized mice by Kohler and Milstein in 1975 (Nature 256: 495–497, 1975) demonstrated for the first time that it was possible to obtain a continuous cell line making homogeneous (so-called "monoclonal") antibody. Since this seminal work, much effort has been directed to the production of various hybrid cells (called "hybridomas") and to the use of the antibody made by these hybridomas for various scientific investigations.

The analysis of lymphocyte populations in human lymphoid tissues has been greatly facilitated by the availability of monoclonal antibodies directed against lymphoid differentiation antigens. These reagents have been used to localize lymphocyte subsets topographically in the lymph node, spleen, and thymus and to phenotype lymphoid malignancies for the diagnosis and classificaton of the non-Hodgkin's lymphomas and leukemias.

An increasing number of monoclonal antibodies directed at B-cell surface antigens have been reported. Among the commercially available products are monoclonal antibodies to each of the heavy and light chain immunoglobulin classes. Other available reagents include BA-1 (Abramson, C. S., Kersey, J. H., and LeBien, T. W. *J. Immunology* 125: 83–88, 1981), B1 (Nadler, L. M., Ritz, J., Hardy, K., Pesando, J. M. *J. Clin. Invest.* 67: 134–140, 1981), B2 (Nadler, L. M., Stashenko, P., Hardy, R., Van Agthoven, A., Terhorst, C., and Schlossman, S. F. *J. Immunol.* 126: 1941–1947, 1981), BL1, BL2, and BL3 (Wang, C. Y., Azzo, W., Al-Katib, A., Chiorazzi, N., and Knowles, D. M. *J. Immunol.* 133: 684–691, 1984), OKB1, OKB2, OKB4, and OKB7 (Mittler, R. S., Talle, M. A., Carpenter, K., Rao, P. E., and Goldstein, G. *J. Immunol.* 131: 1754–1761, 1983) and others. Although these monoclonal antibodies have been found to identify B-cell differentiation antigens, many cross-react with non-lymphoid tissues, have relatively low avidity of binding, or are directed against antigens which are shed into the blood. Hence, B-Cell specific monoclonal antibodies with in vivo diagnostic or therapeutic potential have not been described to date.

SUMMARY OF THE INVENTION

A hybridoma clone, designated Lym-1, was produced from the fusion of primed mouse splenocytes and mouse myeloma NS-1 cells. Hybridoma Lym-1 produced a murine IgG2a monoclonal antibody which recognizes a 31, 32, 33, and 35 kilodalton cell surface protein expressed in normal and malignant B lymphocytes. Immunoperoxidase staining of a panel of normal human tissues shows that Lym-1 reacts with germinal center and mantle zone B lymphocytes and interdigitating histiocytes of the lymph node, medullary dendritic cells of the thymus, and weakly with surface epithelium of the colon. A subset of peripheral blood B cells are positive and no reactivity has been observed in human bone marrow by flow cytometric analysis. The antigen recognized by Lym-1 is not shed from the surface of lymphoma cells either in cell culture or in patients and is not modulated after Lym-1 binding. Lym-1 itself has been shown to have high avidity to human lymphoma cells in vivo as demonstrated by radionuclide binding studies in lymphoma patients using I-123 conjugates. Binding to normal tissues such as the bone marrow, spleen, lymph node, liver, kidney, lung, or central nervous system has not been demonstrated in over 30 patients studied. Lym-1 has further been found to be highly stable to radionuclide conjugation methods and may be prepared as $F(ab')_2$ or $F(ab)$ fragments without significant loss of antibody activity. Collectively, these data suggest that Lym-1 will be an appropriate reagent for in vivo diagnosis and therapy of the human B-cell lymphomas and leukemias.

DETAILED DESCRIPTION

The antigenic preparation used in obtaining the hybridoma Lym-1 consisted of the nuclei of the human lymphoma cell line Raji, which cell line is generally available in the United States and other countries. See Epstein, et al. in *J. Immunol.* 133: 1028–1036, 1984 for the nuclei preparation procedure. The purified Raji nuclei were used to prepare the murine hybridoma according to well known procedures. Briefly, hybridoma clone Lym-1 was produced by the fusion of mouse myeloma NS-1 cells and BALB/c splenocytes obtained from a mouse hyperimmunized with the nuclei of Raji cells.

The monoclonal antibodies produced by the hybridoma Lym-1 were tested to determine the properties and specificity of Lym-1. These tests and the results are described below.

For the purpose of this patent application, cultures of the hybridoma Lym-1 have been placed on deposit with the American Type Culture Collection, 12301 Parklawn Drive Rockville, Md. 20852. Hybridoma Lym-1 has been assigned the ATCC accession No. HB 8612. This deposit has been conformed to the requirements of the Budapest Treaty. The primary characteristics of hybridoma Lym-1 are as follows:

1. Origin:

It was produced by fusion of NS-1 mouse myeloma cells with BALB/c mouse splenocytes primed with Raji human lymphoma nuclei.

2. Cultivation:

The Lym-1 hybridoma can be cultivated in RPMI-1640 medium containing 15% fetal calf serum, 100 units/ml penicillin-G, and 100 μg/ml streptomycin sulfate.

3. Properties:

The Lym-1 hybridoma is not phytopathogenic and is not known to have any dangerous properties. It is tumorigenic in BALB/c mice.

4. Antibody:

Lym-1 produces a murine IgG2a monoclonal antibody which specifically stains the germinal center, mantle zone, and interfollicular histiocytes of human lymph nodes and derived malignancies. It is negative on T- cells, myeloid cells, and other human tissues studied to date. Lym-1 recognizes a 31, 32, 33, and 35 kilodalton cell membrane protein in Raji cells.

5. Testing:

The production of Lym-1 antibody by the hybridoma cells can be tested by indirect immunofluorescence on viable cells or 2% paraformaldehyde fixed B-cell lines, such as Raji, or by immunoperoxidase staining on frozen sections of human lymph nodes.

The Lym-1 hybridoma may be propagated in vitro at an initial cell concentration of $2 \times 10^5$ cells/ml in RPMI-1640 medium containing 15% fetal calf serum, 100 units/ml penicillin-G, and 100 μg/ml streptomycin sulfate. The cells are grown in stationary suspension culture at 37° C. in a well-humidified 5% $CO_2$ incubator and are transferred every 3–4 days.

Using the culturing procedure described above, the Lym-1 antibody may also be produced. The antibody is obtained by centrifuging the cell culture medium at 1,000 rpm for 10 minutes at 4° C. to pellet the cells. The supernatant, which contains approximately 10 μg/ml of IgG2a monoclonal antibody, is then frozen at −20° C. in small aliquots for use in the immunofluorescence and immunoperoxidase procedures.

To obtain larger yields of higher concentration Lym-1 antibody for the radioimmunolocalization studies, the hybridoma may be injected into BALB/c mice. The injected hybridoma will cause the formation of antibody-producing tumors after a suitable incubation time, which will result in a high concentration of the desired antibody in the bloodstream and the peritoneal exudate (ascites) of the host mouse. The Lym-1 antibody is recovered from the mice by removing the ascites fluid with a needle and syringe. The ascites is then spun at 1,000 rpm for 15 minutes at 4° C. to pellet the cells and the supernatant is filtered sequentially through a 0.8 micron and 0.22 micron filter units to remove residual debris. Using sterile technique, the filtered ascites is then stored at −80° C. for long-term stability. From this preparation, approximately 2–3 mg/ml of IgG2a can be recovered and purified by standard methods. Literature references describing the foregoing procedures are: Hoogenraad, N., Helman, T., and Hoogenraad, J.: *J. Immunol. Methods*, 61: 317–320, 1983. Goding, J. W., *J. Immunol. Methods*, 39: 285–308, 1980.

EXPERIMENTAL EXAMPLES

The scientific basis of the present invention will be more fully understood from the following description of the research investigations which led to the invention.

MATERIALS AND METHODS

Antigen Preparation

Nuclei from the Raji cell line were prepared. 2 ml of packed cells were thawed and washed once with Ca/PIPES buffer (0.01M $CaCl_2$, $2 \times 10^{-3}$M piperazine-N,N'-bis(2-ethanesulfonic acid) in a 50-ml centrifuge tube. The sediment was then resuspended in 40 ml of Ca/PIPES buffer and thoroughly homogenized by using a motor-driven Teflon pestle to disrupt the swollen cells. The nuclei were then sedimented and resuspended in Ca/PIPES buffer containing 1% Nonidet P-40. The nuclei were then rehomogenized and checked by phase contrast microscopy to be free of contaminating cytoplasmic and membranous debris. Nuclei were then washed twice in Ca/PIPES buffer to remove the detergents, resuspended in 10 ml of PBS, and sonicated three times for 15-sec intervals to produce a more homogeneous suspension. The nuclei preparations were then frozen in 1-ml aliquots at −85° C. until use.

Immunization Protocol

A 1-ml aliquot of the nuclear preparation was thawed, resonicated to reduce viscosity, and emulsified in 1.5 ml of complete Freund's adjuvant (Difco Laboratories, Detroit, Mich.) by using two glass syringes and a 20-gauge microemulsifying needle (Bolab). Three 10-wk-old BALB/c female mice were injected subcutaneously at multiple sites by using a 22-gauge needle and glass syringe. Two weeks later, the mice were reinoculated as above except the nuclear extracts were prepared in incomplete adjuvant. Ten days later, the mice received a third inoculation of antigen, this time without adjuvant and by i.p. injection. Four days later, the mice were sacrificed by cervical dislocation and the spleens were removed by aseptic techniques.

Cell Fusion And Cloning Procedures

Spleen cells were fused with 8-azaguanine-resistant mouse myeloma NS-1 cells at a ratio of 5:1, respectively, by using 40% polyethylene glycol 1540 m.w. as described by de St. Groth and Scheidegger, *J. Immunol. Methods*, 35: 1, 1980. Culture supernatants from wells with active cell growth were tested by indirect immunofluorescence with fixed cell preparations as described below. Positive cultures were cloned twice on 0.5% Noble agar containing RPMI 1640 medium, 20% fetal calf serum, and antibiotics, as described by Epstein and Kaplan, *Cancer Res.*, 39: 1748, 1979.

Serologic Characterization of Monoclonal Antibody Isotypes

Hybridoma supernatants from 4-day cultures were concentrated 10 to 20x in 15 minicon concentrators (Amicon, Lexington, MA) and tested in double diffusion Ouchterlony plates against rabbit anti-mouse immunoglobulin heavy chain specific antisera. The precipitin bands were read after 2 to 3 days of incubation in a well-humidified 37° C. incubator.

Live Cell Indirect Immunofluorescence.

Cells were washed twice with PBS (0.2 g $KH_2PO_4$, 0.1 g $CaCl_2.2H_2O$, 1.15 g $Na_2HPO_4$, 0.1 g $MgCl_2.6H_2O$, 0.2 g KCl, 8.0 g NaCl/liter) containing 1 mg/ml bovine serum albumin (BSA: RIA grade, Sigma Chemical, St. Louis, MO) and 0.02% sodium azide. Single cell suspensions containing $1 \times 10^6$ cells were incubated for 30 min with 100 μl of monoclonal antibody supernatant at 4° C. Cells were then washed to remove excess antibody and incubated with a 1/20 dilution of fluorescein-conjugated goat anti-mouse IgGF(ab')2 fragment specific (Cappel, Cochranville, PA) for 30 min at 4° C. After two additional washes, two drops of mounting solution composed of 1:1 glycerol and PBS, pH 8.0 and 2% paraformaldehyde (#4018, Polysciences, Warrington, PA) were added to each tube. The cells were mounted onto a glass slide and examined within 24 hours by epifluorescence microscopy with a Leitz Orthoplan microscope with a ploemopak 2.1 fluorescence illuminator, HBO 100 mercury lamp, and 50x water immersion objective. A minimum of 200 cells were examined for immunofluorescence staining by two independent observers. Supernatant from NS-1 myeloma cultures was used as a control to determine the background staining of each cell line.

Fixed Cell Indirect Immunofluorescence

To examine cells for the presence of intracellular antigens, fixed cell preparations were used. Cells were washed twice with PBS containing 1 mg/ml BSA and 0.02% sodium azide and were pipetted dropwise at a concentration of $5.0 \times 10^6$ cells/ml onto Teflon-coated printed microscope slides containing 10 5-mm wells/slide. After the cells settled to the surface of the glass, the overlying fluid was quickly removed by aspiration and the cells were dried to the slide by a gentle stream of warm air. The slides were then immediately fixed in 2% paraformaldehyde in PBS for 15 min at room temperature. After fixation, the slides were rinsed in PBS and placed in acetone at $-20°$ C. for 3 min to make the cells permeable. After a final rinse to remove the acetone, the slides were stored at 4° C. in PBS containing 0.02 % sodium azide.

For the immunofluorescence assay, 35 μl of hybridoma supernatant were pipetted onto each well of the printed microscope slide preparations. After 60 min of incubation at 37° C. in a humidified chamber, the slides were rinsed three times in PBS and again incubated for 30 min at 37° C. with 20 μl of a 1/20 dilution of fluorescein conjugated goat anti-mouse IgGF(ab')$_2$ fragment specific. The slides were then rinsed three times in PBS, counterstained with Evans blue for 5 min at room temperature by using a freshly prepared solution containing 50 μl of a 1% stock solution of Evans blue in 80 ml of PBS, rinsed a final time in PBS, and mounted with coverslips by using a 1:1 solution of glycerol and PBS, pH 8.0.

Immunoperoxidase Staining

Frozen sections were prepared from human tissue biopsies obtained from the Section of Surgical Pathology, Northwestern Memorial Hospital, from specimens submitted from pathologic diagnosis. The sections were stained with the monoclonal antibody Lym-1 by using the avidin-biotin complex immunoperoxidase staining procedure as described by Hsu, et al. *J. Histochem. Cytochem.* 29: 577–580, 1981. For these experiments a ½ dilution of Lym-1 supernatant was used. As a negative control, NS-1 supernatant which is unreactive in frozen sections, was used with each run.

Radioimmunoassay for the Detection of Shed Antigen

In order to determine if the antigen detected by Lym-1 is shed from the surface of human lymphoma cells in vitro and in patients, a sandwich solid phase radioimmunoassay was developed. In this assay, purified Lym-1 is attached to plastic immulon wells by incubation for 1 hr at room temp. After removing excess antibody by washing with PBS, the wells are further incubated for 30 min. at room temperature with PBS containing 10 mg/ml bovine serum albumin to block the surface of the immulon wells from further protein binding. After removing the excess BSA, concentrated supernatant from cultured Raji cels, Raji membrane preparations (positive control), or human serum from lymphoma patients were incubated for 30 minutes at room temp. After washing, 100,000 cpm of I-125-Lym-1 was added to determine the amount of bound antigen. After a 30 minute incubation period and thorough washing with PBS, the wells were counted in a gamma counter.

Antigen Modulation Studies

Antigenic modulation after Lym-1 binding was determined by indirect immunofluorescence procedures as described by Ritz et al. (*Blood* 58: 141-152, 1981).

Lym-1 Purification

A summary of Lym-1 purification is described as follows:
1. raise ascites in pristane primed BALB/c mice.
2. harvest ascites aseptically from peritoneal cavity.
3. remove cells by centrifugation (1,500 rpm for 20 min).
4. filter to sterilize and remove debris (0.2 micron).
5. 50% ammonium sulfate precipitation.
6. dialysis against PBS overnight at 4° C.
7. affinity purification on Protein-A sepharose. Eluate at pH 5.6–5.7.
8. dialyze against PBS overnight at 4° C.
9. ultracentrifuge at 30,000 rpm for 1 hr at 4° C.
10. membrane filter (0.2 micron).
11. store in aliquots at $-80°$ C. until use.

F(ab) and F(ab')$_2$ fragments of the above preparation were prepared by papain and pepsin digestions, respectively, using standard procedures.

Radioiodinatipn Procedures

For the animal studies, purified Lym-1 was radiolabeled by a solid phase system using Iodogen (Pierce Chemical, Rockford, IL). In a typical reaction, Iodogen (0.5–2.0 μg) was plated into test tubes using methylene chloride. A mixture of Lym-1 (0.1–1.0 mg/ml) and I-131 sodium iodide (50–500 μCi) was added to the tubes containing Iodogen and incubated at 4° C. for 15 min. The reaction was terminated by decanting the solution. The radiolabeled Lym-1 was purified using gel exclusion chromatography with Biogel P-10, 50–500 mesh (Bio-Rad Labs, Richmond, CA).

For the patient studies, Lym-1 and F(ab) and F(ab')$_2$ fragments were radiolabeled with I-123 using a modified chloramine T method (Mills, S. L., DeNardo, S. J. , DeNardo, G. L., Schlom, J., Epstein, A. L., and Lagunas-Solar, M., *J. Nuclear Medicine,* submitted). I-123-Lym-1 was evaluated by cellulose acetate (pH 8.6) electrophoresis and by HPLC-TSK 3000 chromatography.

Lym-1 Binding Assay

The radioimmunoreactivity of the radiolabeled monoclonal antibody was determined using a live cell assay consisting of $1 \times 10^6$ Raji cells. CEM cells from a T-cell acute lymphoblastic leukemia cell line were used to assess the extent of non-specific binding. Purified radiolabeled Lym-1 was added to 1 ml of the respective cell suspension at antigen excess and incubated at room temperature for 60 minutes. The cell suspension was then washed with 3x with PBS and counted using appropriate gamma scintillation spectrometry to assess the degree of binding.

Radioimaging of Tumor-Bearing Mice

Athymic nude mice, each bearing a right thigh human lymphoma induced by an intramuscular injection of $1 \times 10^7$ Raji cells were given Lugols solution orally 24 hr. prior to initiation of the study. Between 150–400 μCi of I-131-Lym-1 was then injected intravenously into the heterotransplanted nude mice. Posterior gamma scintillation images (100,000 counts) were obtained up to 7 days after injection using a gamma scintillation camera with a pinhole collimator interfaced to a computer system. Immediately after animal imaging, an appropriate I-131 standard was counted with the same geometry in order to quantitate the animal data. At 7 days after injection, the animals were sacrificed and organ biodistribution studies were performed using appropriate gamma scintillation counting.

Radioimaging of Cancer Patients

Volunteer breast cancer and lymphoma patients were injected with 1-5 mCi of I-123 labeled Lym-1 or fragments. Serum sample obtained at 5 min, 30 min, 1 hr, 2 hr, 6 hr, 18 hr, 24 hr, and 48 hr post-injection were evaluated by HPLC-TSK 3000 in order to assess the size of the circulating radiolabeled molecules. Urine samples were also taken to determine the total I-123 excreted over 24, 48, and 74 hr, post-injection. On selected urine samples, HPLC-TSK 3000 analysis was performed to examine the size of the I-123 molecules being excreted. Planar images of the head, chest, and anterior and posterior abdomen were obtained for 750,000 counts with a medium energy collimator at 0.2 hr, 4-6 hr, and 18-24 hr post-injection. Single photon emission tomographic images (SPECT) were obtained at 2-4 hr and 24 hr post-injection over the chest and abdomen (64 views on an 128×128 matrix). Computer reconstruction and attenuation corrections were performed on these images and uptake was compared to I-123 calibration pin phantom (Macey et al., *J. Nuclear Med.* 25:105, 1984).

NMR Enhancement Studies

In collaboration with Dr. Michael McNamara at the University of California at San Francisco NMR Research Institute, Lym-1 has been conjugated to gadolinium using anhydrous DTPA. Raji lymphoma implants in nude mice were used to study the effects of gadolinium conjugated Lym-1 on NMR relaxation times and image enhancement.

Immunotoxin Conjugation

In collaboration with Clin Midy/Sanofi in Montpellier, France, Dr. Guy Laurent has conjugated purified Lym-1 with ricin toxin A chains to determine its cytotoxic effects on three target cell lines (Raji, Daudi, and SB). Using a protein synthesis inhibition assay, the IC50 (amount of A chain to obtain 50% inhibition of leucine incorporation), was measured in order to determine the potential effectiveness of this immunotoxin.

RESULTS

Hybridoma clone Lym-1 was produced by the fusion of mouse myeloma NS-1 cells and BALB/c splenocytes obtained from a mouse hyperimmunized with nuclei from Raji cells. Isotypic analysis revealed that monoclonal antibody Lym-1 was of the IgG$_2$ heavy chain subclass. The Lym-1 antibodies were identified by indirect immunofluorescence techniques with the use of paraformaldehyde-acetone-fixed cell preparations.

The reactivities of monoclonal antibodies Lym-1 on established human malignant lymphoma and leukemia cel lines are shown in Tables I and II, respectively.

TABLE 1

| Cell Line | Lym-1[a] |
|---|---|
| Reactivity of Lym-1 with human malignant lymphoma cell lines by indirect immunofluorescence | |
| Burkitt's lymphoma | |
| Raji | +[b] |
| EB3 | − |
| RAMOS | − |
| SU-AmB-1 | − |
| SU-AmB-2 | + |
| NU-AmB-1 | − |
| NK-9 | − |
| Diffuse histiocytic lymphoma | |
| SU-DHL-1 | − |
| SU-DHL-2 | − |
| SU-DHL-4 | − |
| SU-DHL-5 | − |
| SU-DHL-6 | + |
| SU-DHL-7 | + |
| SU-DHL-8 | + |
| SU-DHL-9 | + |
| NU-DHL-1 | + |
| U-937 | − |
| Undifferentiated lymphoma | |
| NU-DUL-1 | − |

[a]Fixed cell indirect immunofluorescence assay.
[b]Data expressed as (−) negative, (+) positive.

TABLE II

Reactivity of Lym-1 with human leukemia and lymphoblastoid cell lines by indirect immunofluorescence

| Cell Line | Lym-1[a] |
|---|---|
| Acute lymphoblastic leukemia | |
| T Cell | |
| Molt-4 | −[b] |
| CEM | − |
| HSB-2 | − |
| HPB-ALL | − |
| JM | − |
| Null cell | |
| REH | + |
| NALL-1 | − |
| KM-3 | − |
| B-cell | |
| BALM-2 | + |
| NALM-6 (pre-B) | − |
| NALM-1 (pre-B from CML) | − |
| Myeloid leukemia | |
| K562 (erythroid-CML) | − |
| HL-60 (promyelocytic) | − |
| ML-2 (myeloid) | − |
| TPH-1-0 (monocytic) | − |
| KG1 (myeloid) | − |
| Myeloma | |
| U-266 | − |
| ARH-77 | + |
| Lymphoblastoid | |
| BL-1 | − |
| NU-LB-1 | + |
| NU-LB-2 | + |

[a]Fixed cell indirect immunofluorescence assay.
[b]Data expressed as (−) negative; (+) positive.

In Table III, the staining reactivity of Lym-1 on human malignant lymphoma and chronic lymphocytic leukemia biopsies is shown. Indirect immunofluorescence studies showed that Lym-1 was positive on the majority of B-cell derived tumors.

TABLE III

Indirect immunofluorescence staining of human lymphoma and chronic lymphocytic leukemia biopsy cells

| Diagnosis | Lym-1 Reactivity (positive cases/total cases) |
|---|---|
| Lymphoma[a] (frozen sections of lymph node biopsies) | |

TABLE III-continued
Indirect immunofluorescence staining of human lymphoma and chronic lymphocytic leukemia biopsy cells

| Diagnosis | Lym-1 Reactivity (positive cases/total cases) |
|---|---|
| well-differentiated lymphocytic | 1/3 |
| poorly-differentiated lymphocytic | 1/5 |
| mixed lymphocytic and histiocytic | 8/9 |
| histiocytic (B-cell type) | 12/17 |
| T-cell | 0/2 |
| Leukemia (cytospins of peripheral blood) Chronic lymphocytic | |
| B-cell type | 4/10 |
| T-cell type | 0/5 |

*a*Rappaport classification.

The immunoperoxidase staining reactivity of Lym-1 on frozen sections of normal human biopsy tissues is shown in Table IV. Lym-1 was found to be specific to B-cell lymphocytes and histiocytes in lymphoid tissues. No reactivity was demonstrated in human bone marrow or in non-lymphoid human organs.

TABLE IV
Reactivity of Lym-1 with normal human tissues

| Tissue | Lym-1 Reactivity | |
|---|---|---|
| lymph node | + | B cell zones |
| tonsil | + | B cell zones |
| thymus | + | medullary dendritic cells |
| bone marrow* | − | |
| blood* | + | subset of B lymphocytes |
| adrenal | − | |
| brain | − | |
| breast | − | |
| colon | + | surface epithelium, macrophages |
| heart | − | |
| liver | − | |
| lung | − | |
| pancreas | − | |
| salivary gland | − | |
| skin | − | (macrophages positive) |
| skeletal muscle | − | |
| smooth muscle | − | |
| thyroid | − | |

*Determinations made by flow cytometric analysis on viable cells in suspension.

The immunoreactivity of Lym-1 on human solid tumor cell lines was determined by indirect immunofluorescence techniques on fixed cell preparations. As shown in Table V, Lym-1 was not found reactive on the cell surface of any of the 26 cell lines tested, but did have weak reactivity on a small number of cell lines in the cytoplasm or nucleus.

TABLE V
Immunoreactivity of Lym-1 with human solid tumor cell lines

| Solid Tumors | Lym-1 Reactivity | |
|---|---|---|
| CaCL-74-36 (melanoma) | −*a* | |
| BM-166 (neuroblastoma) | − | |
| Y79 (retinoblastoma) | − | |
| HeLa (ovarian carcinoma) | − | |
| SU-CCS-1 (clear cell sarcoma) | − | |
| Colo 38 (melanoma) | − | |
| C-399 (colon carcinoma) | − | |
| A-172 (glioblastoma) | − | |
| NCI-H69 (small cell carcinoma of lung) | − | |
| IMR-5 (neuroblastoma) | − | |
| Hutu-80 (colon carcinoma) | − | |
| HT-29 (colon carcinoma) | − | |
| 734B (breast carcinoma) | − | |
| SW-80 (rhabdomyosarcoma) | − | |
| SW-1503 (mesothelioma) | − | |
| SW-733 (papillary carcinoma of bladder) | + | weak cytoplasmic speckling |
| U118-MG (glioblastoma) | + | sparce cytoplasmic speckling |
| SW-872 (liposarcoma) | + | discrete nuclear speckling |
| SW-780 (transitional cell carcinoma of bladder) | − | |
| SW-1045 (synovial cell carcinoma) | − | |
| SW-608 (astrocytoma) | + | cytoplasmic speckling |
| SW-1353 (chondrosarcoma) | − | |
| SW-451 (squamous cell carcinoma of esophagus) | + | nuclear speckling |
| SW-156 (hypernephroma) | − | |
| NU-04 (glioblastoma) | + | nuclear speckling |
| SW-579 (squamous cell carcinoma of thyroid) | − | |

*a*−: negative; +: positive by indirect immunofluorescence microscopy on fixed cell preparations.

Table VI below summarizes the major characteristics of Lym-1 antibody.

TABLE VI
Characterization of Monoclonal Antibody Lym-1

| | Lym-1 |
|---|---|
| Immunogen | Raji nuclei |
| Isotype | IgG2a |
| Antigen | 31,32,33,35 kilodalton protein |
| Antigen site | cell surface |
| Lymphoid Reactivity | |
| lymph node and tonsil | B-cell zones and histiocytes |
| bone marrow | none |
| blood | subset of B lymphocytes |
| thymus | medullary dendritic cells |
| Non-Lymphoid Reactivity | none |
| Tumor Specificity | B-cell lymphomas and leukemias |

Antigenic modulation experiment using Raji cells showed that the antigen recognized by Lym-1 does not modulate on the cell surface but is stably expressed for several days. A sandwich radioimmunoassay technique used to determine if the antigen detected by Lym-1 was shed from the surface of human lymphoma cells either in vitro or in patients clearly gave negative results as shown in Table VII.

TABLE VII
DETECTION OF SHED ANTIGEN BY RADIOIMMUNOASSAY

| Antigen Source | Radioimmunoassay | 1-125-Lym-1 Binding(cpm)* |
|---|---|---|
| Raji cells (1 × 10$^6$) | live cell | 51,582 |
| Raji membranes | solid phase, direct | 6,060 |
| Raji membranes | solid phase, sandwich | 19,274 |
| Raji supernatant (20 × conc.) | solid phase, sandwich | 619 |
| Lymphoma patient sera | | |
| #1 | solid phase, sandwich | 115 |
| #2 | " | 111 |
| #3 | " | 168 |
| #4 | " | 385 |
| #5 | " | 269 |
| CEM cells (1 × 10$^6$) | live cell | 214 |

*1 × 10$^6$ cpm/test

Animal radioimaging studies with Lym-1 showed that Lym-1 bound specifically and rapidly to the Raji tumor implant with essentially no binding seen to normal mouse organs. Biodistribution studies at day 7 with I-131-Lym-1 antibody is shown below in Table VIII.

TABLE VIII

Biodistribution of I-131-Lym-1 in heterotransplanted nude mouse

| organ | % injected dose | % injected dose gram |
|---|---|---|
| blood | — | 1.441 |
| heart | 0.048 | 0.355 |
| lung | 0.088 | 0.335 |
| liver | 0.403 | 0.296 |
| spleen | 0.044 | 0.720 |
| kidney | 0.159 | 0.382 |
| tumor | 8.216 | 3.191 |

PATIENT RADIOIMAGING STUDIES

In studies performed over the last 20 months in collaboration with Dr. Sally DeNardo at the University of California at Davis, 5 breast cancer patients (negative control) and 25 lymphoma patients have been imaged using planar films and SPECT instrumentation after injection of I-23-Lym-1 radioconjugate (1–5 mCi). Examples of the lymphoma lesions were successfully obtained in all 25 lymphoma patients at 4 hr and 18 hr post-injection. In the 5 breast cancer patients and in all lymphoma patients, binding of I-123-Lym-1 to normal tissues was not seen. Metastatic tumors identified by biopsy, by NMR or CAT scan, or radiographically were successfully imaged with I-123-Lym-1. Unsuspected tumor, such as those in the bone marrow or occult locations were seen in some patients. HPLC analysis showed that I-123-Lym-1 remained unbound and free in the patient circulation conclusively showing the absence of circulating antigen. The antibody was principally secreted as F(ab) fragments by the kidney. Non-specific uptake of I-123-Lym-1 by the liver could be avoided by preloading the patients with 5 mg of cold Lym-1 prior to the injection of radiolabeled antibody. Whole antibody as well as F(ab) and F(ab')$_2$ fragments conjugated to I-123 were used successfully to image lymphoma lesions in these patients. No anti-mouse immune response and no adverse side effects were noted in any of the patients, even those receiving multiple injections over a several months period.

NMR Studies

Gadolinium conjugated Lym-1 was found to shorten the NMR relaxation times and hence produce enhanced NMR images in Raji implants in nude mice 3 days after injection. This is the first successful demonstration of NMR enhancement of tumors using spim labeled conjugated monoclonal antibodies. After gadolinium conjugation with DPTA, over 90% of the antibody reactivity was retained as shown by the live cell binding assay.

IMMUNOTOXIN STUDIES

An IC50 of $10^{-10}$ was obtained with ricin toxin A chain conjugated to Lym-1. By comparison, an anti-HLA-Dr antibody-ricin A conjugate had a 2 log higher IC50. The lower IC50 of Lym-1 may be due to the fact that the immunotoxin is not effectively entering the tumor cell as is shown for antibodies with modulating antigens.

In summary, the advantages of Lym-1 as an in vivo diagnostic and therapeutic reagent aare shown below.

TABLE IX

ADVANTAGES OF LYM-1 AS A RADIOIMAGING AND IMMUNOTHERAPEUTIC REAGENT

Antigen
1. small antigen reservoir
2. not shed or modulated
3. expressed on the majority of B-cell lymphomas and leukemias Antibody
1. highly stable after radiolabeling or spin labeling procedures
2. radioimages lymphomas but not normal lymphoid organs
3. radiolabeled antibody is excreted by kidney
4. does not complex in serum of patients by H.P.L.C. analysis
5. is retained by lymphomas for long periods of time (7 days in mouse model)
6. can be used to shorten NMR relaxation times and give tumor enhancement by NMR
7. can be used theoretically to deliver a therapeutic dose of radiation to tumor tissue without significant toxicity to normal organs or tissues
8. does not appear to produce an anti-mouse response in lymphoma patients
9. does not produce toxic effects in patients

I claim:

1. The hybridoma cell line deposited under ATCC Accession No. HB 8612.

2. The monoclonal antibody produced by the hybridoma cell line deposited under ATCC Accession No. HB 8612 and clones thereof.

* * * * *